(12) United States Patent
Bravo

(10) Patent No.: US 9,387,129 B2
(45) Date of Patent: Jul. 12, 2016

(54) DEVICE AND METHOD TO AVERT ANAL FECAL LEAKAGE

(71) Applicant: Jorge Bravo, Canoga Park, CA (US)

(72) Inventor: Jorge Bravo, Canoga Park, CA (US)

( * ) Notice: Subject to any disclaimer, the term of this patent is extended or adjusted under 35 U.S.C. 154(b) by 130 days.

(21) Appl. No.: 14/330,098

(22) Filed: Jul. 14, 2014

(65) Prior Publication Data

US 2016/0008118 A1    Jan. 14, 2016

(51) Int. Cl.

| | | |
|---|---|---|
| *A61F 2/02* | (2006.01) | |
| *A61F 13/15* | (2006.01) | |
| *A61F 13/20* | (2006.01) | |
| *A61F 13/26* | (2006.01) | |
| *A61F 13/28* | (2006.01) | |
| *A61F 13/475* | (2006.01) | |
| *A61F 2/00* | (2006.01) | |

(52) U.S. Cl.
CPC ......... *A61F 13/15211* (2013.01); *A61F 2/0009* (2013.01); *A61F 13/2011* (2013.01); *A61F 13/266* (2013.01); *A61F 13/28* (2013.01); *A61F 13/4758* (2013.01); *A61F 2013/1513* (2013.01); *A61F 2250/0004* (2013.01)

(58) Field of Classification Search
CPC ..... A61F 2/0004; A61F 2/0009; A61M 29/02
USPC .................. 600/29–32; 128/DIG. 25; 604/913
See application file for complete search history.

(56) References Cited

U.S. PATENT DOCUMENTS

| | | | |
|---|---|---|---|
| 4,686,985 A * | 8/1987 | Lottick | A61M 29/02 604/913 |
| 5,593,443 A | 1/1997 | Carter et al. | |
| 5,695,484 A | 12/1997 | Cox | |
| 5,817,124 A | 10/1998 | Karell | |
| 7,195,619 B2 | 3/2007 | Manasek | |
| 7,360,544 B2 | 4/2008 | Levien | |
| 8,062,277 B2 | 11/2011 | Fleming | |
| 8,353,884 B2 | 1/2013 | Hansen et al. | |
| 8,444,546 B2 | 5/2013 | Shalon et al. | |
| D728,097 S * | 4/2015 | Bravo | D24/141 |
| 2006/0200955 A1 | 9/2006 | Nishihara | |
| 2007/0073099 A1 | 3/2007 | Forsell | |

FOREIGN PATENT DOCUMENTS

DK    WO2007/033683 A1    3/2007

OTHER PUBLICATIONS

Literature from Colorplast Industries, Jul. 24, 2013.

* cited by examiner

*Primary Examiner* — John Lacyk
(74) *Attorney, Agent, or Firm* — Law Office of Ken Dallara; Ken Dallara

(57) ABSTRACT

A device and method to avert anal fecal leakage is disclosed that possess at least two means for the prevention of anal leakage or hemostatic application. The device is inserted internally and is used inside of the rectal cavity for absorption along with a sealing member placed externally against the anus which is designed as a secondary means for the prevention of leakage. An embodiment of the device includes a third sealing means to prevent leakage into the anal canal. The device is constructed to be flexible with a minimum of intrusiveness for the user during use. The device is constructed for one person insertion and removal unless patient or user is incapacitated. Due to its design, the device is capable for use over a wide range of human and certain animal applications.

20 Claims, 6 Drawing Sheets

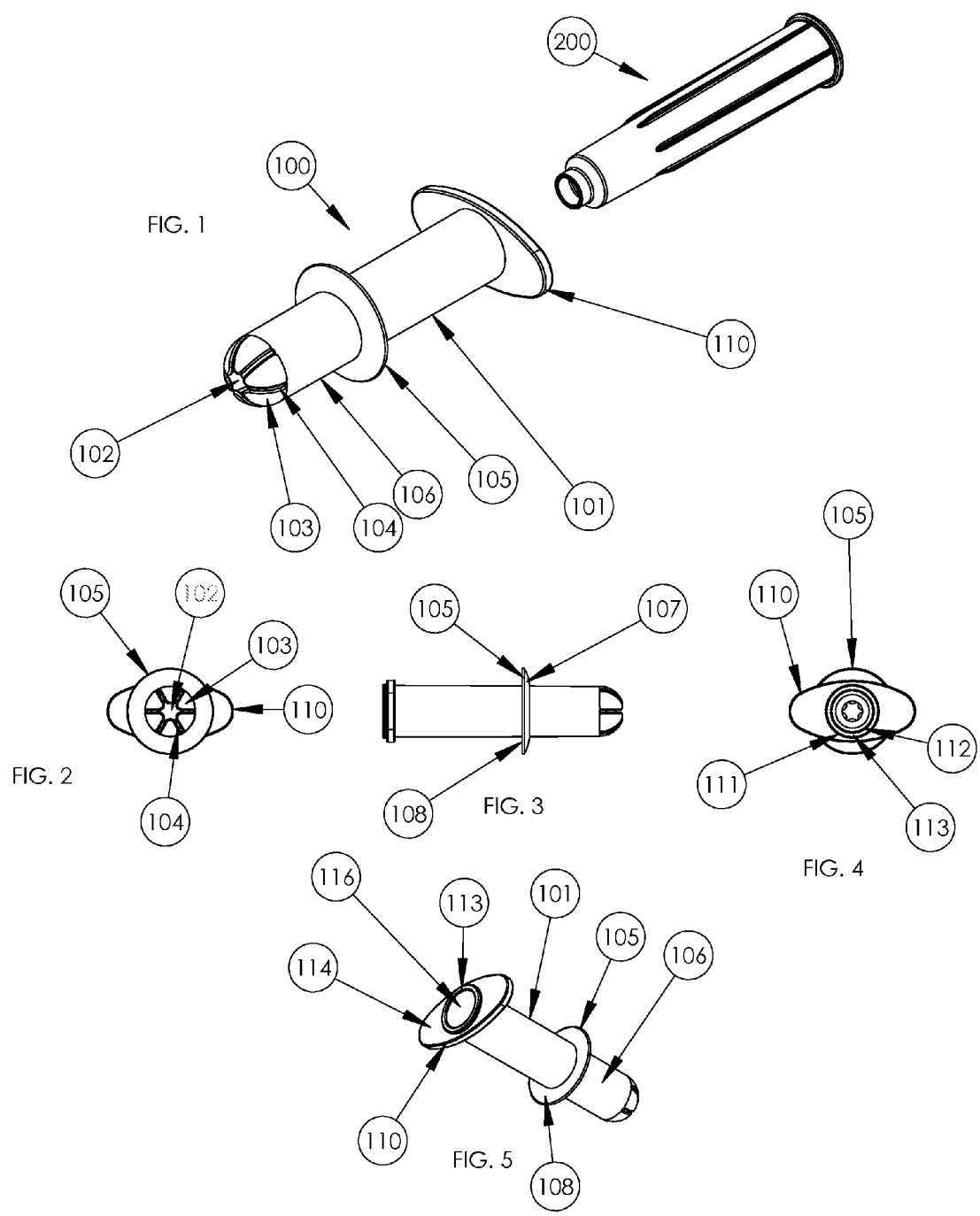

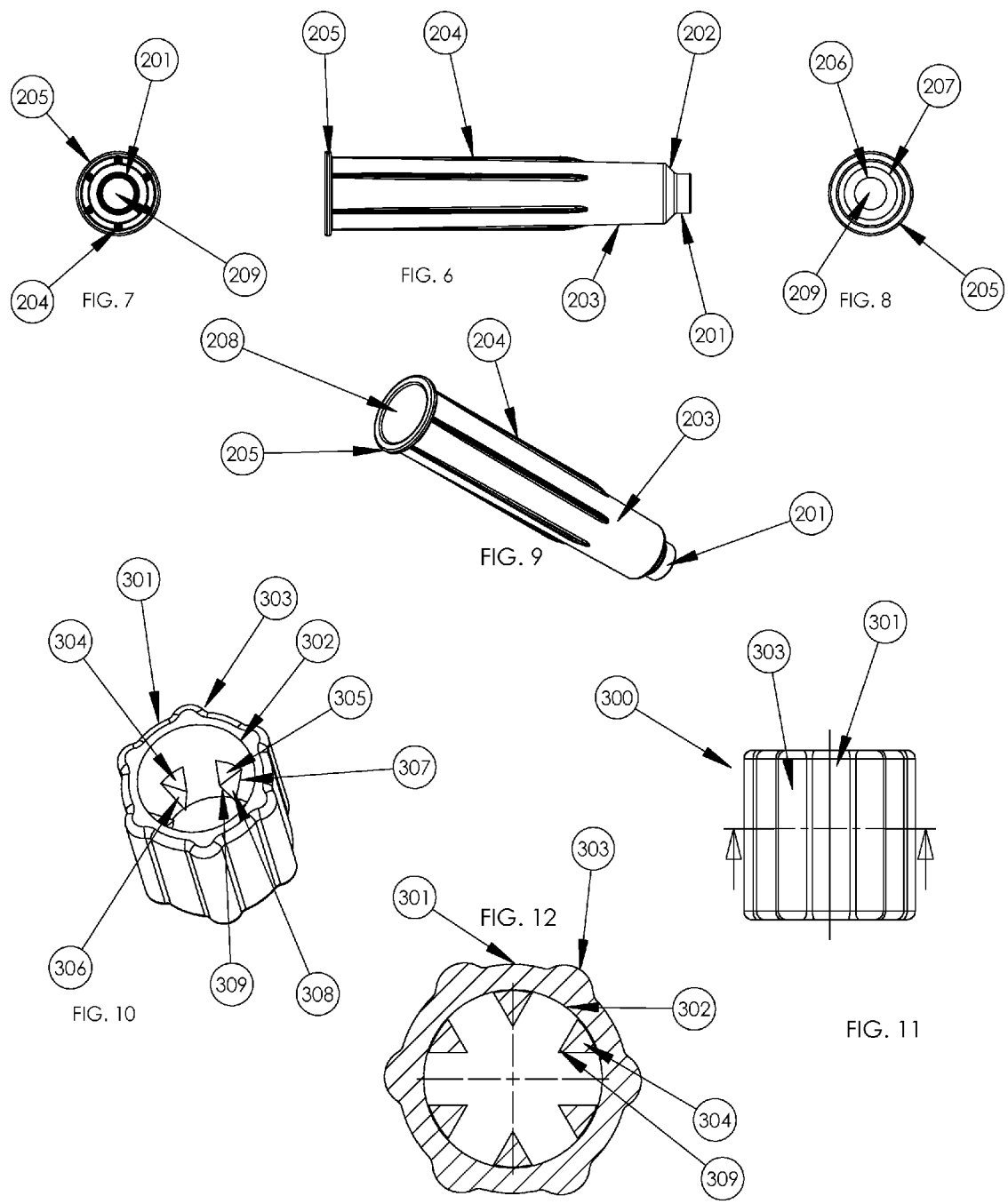

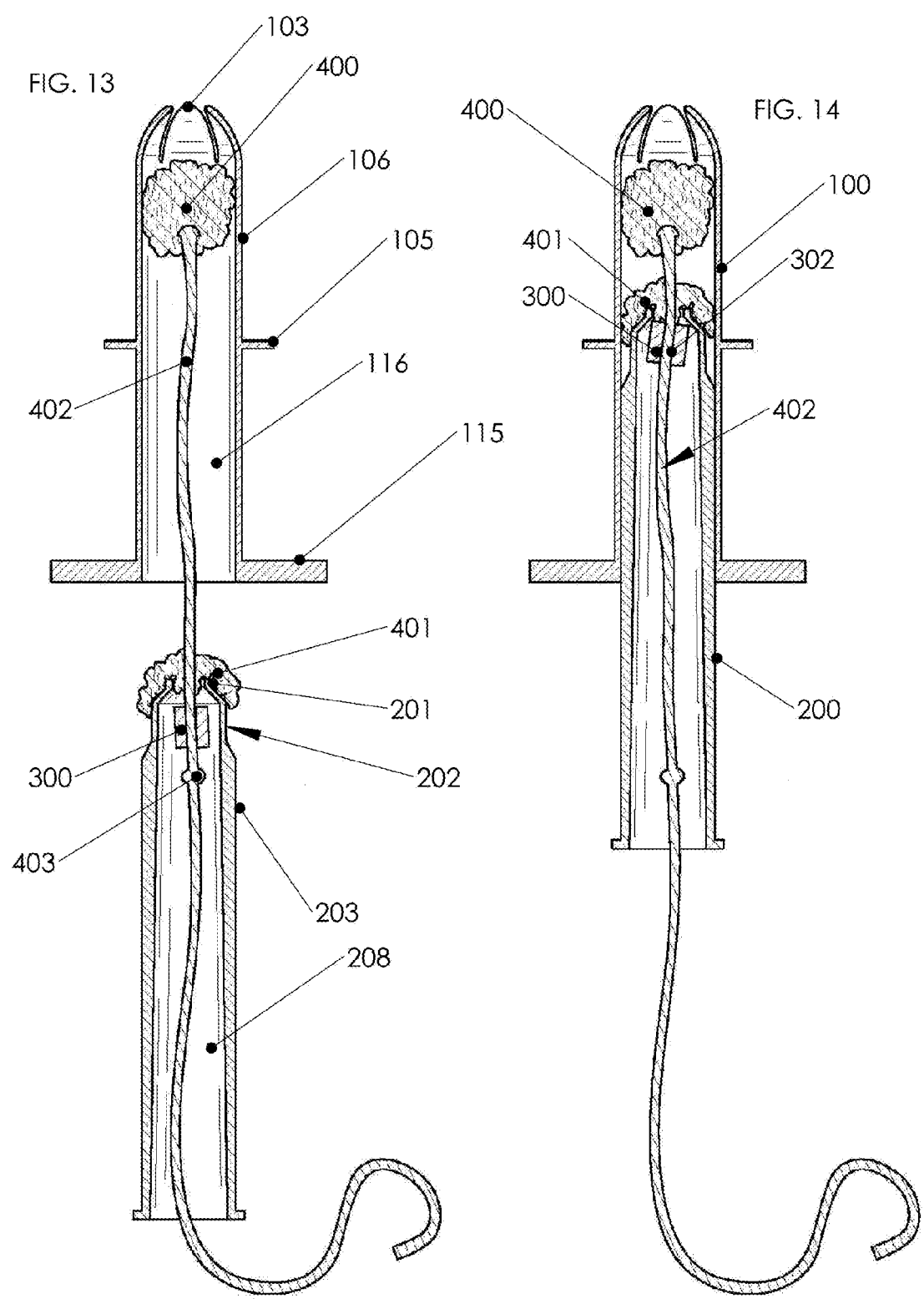

DEVICE AND METHOD TO AVERT ANAL FECAL LEAKAGE

FIELD OF THE INVENTION

The present invention is generally related to the medical field relating to problems that patients who through a variety of reason, suffer from anal fecal leakage. This invention and method for its use is aimed at averting embarrassing situations, isolation of the patient from social events, and reducing the chance of infection and skin damage caused by leakage due to the patient's inability to cause the anal canal to respond to their need to hold fecal matter inside of their body, evacuating at a time and place of their desire.

BACKGROUND OF THE RELATED ART

This invention is designed to help patient who suffer from rectal incontinence. People who suffer from rectal incontinence have an inability to control the muscles that control the evacuation of feces via the anal canal. The aim of any product in this classification of medical devices, especially the device disclosed herein, is to reduce or eliminate the amount of fluid or secretions created by the bowel or stool in those who cannot physically control their bodily functions themselves. The fecal matter and associated fluids can also be created by conditions in which are abnormal such as: Crohns disease, ulcertive colitis, and diarrhea sometimes caused by *Giardia* found in untreated water. The anus is almost incapable of holding fine fluid even for a normal person who does not suffer from Rectal incontinence. Incontinence can also be caused by spinal cord injury, Parkinson's, multiple sclerosis, traumatic brain injury, complications post-surgery, childbirth especially as a result of episiotomy, treatment of the pelvic area with chemotherapies and/or radiation in cancer patients, infections and other causes. Incontinence can also be caused by cognitive/mental disabilities such as severe mental retardation, and severe autism. Due to the nature of the design of this device, and its method for use, this device is also applicable in animals in certain cases as well as in humans.

This invention also has its uses during the embalming and postmortem procedures where leakage is a common occurrence with the buildup of gases and fluids in the body which will eventually escape through the natural orifices as the pressure builds.

In a healthy subject, one's fecal continence is controlled by the voluntary constriction of the external and internal anal sphincters which is a circular band of muscle surrounded by a two flattened planes of muscular tissue and the associated constriction of the interior anal sphincter via its set of muscular tissues surround the anal canal. These muscles are always in a state of tonic contraction but yet have no antagonist muscles to oppose the sphincter muscles that act in opposition to the specific movement generated by the sphincter muscles. The muscles can be further constricted by voluntary movement of the subject causing a further occlusion of the anus, the last area of sealing controlled by the external and internal anal sphincters to prevent accidental discharge.

The anus is the last part of the intestinal tract. It is the final orifice through which stool passes out of the body. The lower half of the anal canal has sensitive nerve endings. There are blood vessels under the lining, and in its mid portion there are numerous tiny, anal glands. There are visceral nerves inside of the anal canal, which are sensory motor nerves, which feel only pressure. This gives the sensation of fullness and therefore one defecates once a certain pressure is reached. Somatic nerves, one of the nerves of parietal sensation or voluntary motion, are located on the exterior of the anal canal and anus and can feel pressure as well as pain. Due to the density of nerves in this region, it is especially important not to have a device that increases pain and discomfort.

The prior art is replete with devices that are used to control anal leakage and can be broken down into three basic categories; 1) devices that are designed to catch the fecal matter as there is no control of the process, 2) devices that attempt to simulate the action of the sphincter muscles and 3) devices meant to stem the tide of the leakage by placing devices into the rectal cavity.

Devices in category one include absorbent undergarments, such as adult diapers or waterproof pants or shorts with liners that can absorb liquid matter. These are mostly designed for uniform solid matter. Some of these garments come with reservoirs to hold the solid matter, but this, only increases the bulkiness and decrease the comfort and ease of use when these reservoirs are attached. These garments are already very uncomfortable and bulky to begin with. Physical movement, let alone exercise, and inability to discretely carry multiple diapers, is greatly limited as these garments are not designed for movements of the legs and pelvis, or they are so restrictive that they prevent normal activities, such as walking, running, swimming and intimacy. In addition, the traditional diaper holds fecal material as stated above, therefor placing the patient at risk for skin breakdown, foul odor and pain. Thinner absorbent pads can be used, such as panty liners, but are not appropriate for anal incontinence as the pads are hard to locate retro-anally into undergarments as the garments will shift between standing and sitting to laying and/or walking positions of the users, thereby creating a false sense that the pads will be in the proper location to absorb. Some pads or patches are adhesively adhered to the user. U.S. Pat. No. 8,353,884 issued to Hansen et al on Jan. 15, 2013 and U.S. Pat. No. 7,195,619 issued to Manasek on Mar. 27, 2007 typify the types of absorbent pads or patches that are available. Both are to be placed onto the garments but by their shape and design, they are capable of being located into a close proximity of the anus and are designed to catch the leakage as it is directed into the pad where absorbent material. The '884 patent provides for a two part device where the absorbent pad is unattached to the flanged part which has the advantages of sealing more closely to the anus and addresses the issues regarding the movement of the pad during exercise and simple movements but is confined to those "low-level incontinence" as those without any control of their bowels will have a much heavier flow at times thereby inundating the pads beyond their capacity.

Another example of this style of pads are designed to prevent the flow from exiting by closely fitting into the perineum region by fitting within the intergluteal or natal cleft, being held in place through the use of adhesives (U.S. Pat. No. 5,695,484 issued to Cox on Dec. 9, 1997) or by contouring an absorbent pad into a shape that coincides with the shape of the individual's intergluteal region. Both of these patents approach the problem of leakage uniquely but still have problems similar to the aforementioned prior art. The pads are difficult to place into the correct region, adhesives are difficult to adhere to often hairy skin areas, perspiration and movement by the user can dislodge the pad easily and will cause embarrassing and unsanitary leakage.

Prior art discloses devices that try to eliminate the leakage from either trying to trick the body into closing their sphincter muscles or have a mechanical means to accomplish the same result. U.S. Pat. No. 7,360,544 issued to Levien on Apr. 22, 2008 details the insertion of a truncated cone and a straight tube with an angled concavity, which allegedly exploits the voluntary inhabitation action and/or simple closure of the anal slit to decrease facial incontinence or soiling whereby the contraction of the external sphincter muscles to hold the tube will cause a relaxation of the rectum thereby increasing the reservoir capacity of the rectum. This patent assumes that one has the control in the muscles but for some reason, one fails to utilize the control, but does not address those situations where one is without any muscle control of the anus or either of the sphincters. U.S. Pat. No. 5,593,443 issued to Cater et al on Jan. 14, 1997 details a surgical procedure where the action of the damaged sphincter muscle is replaced with an inflatable tube which simulates the sphincter closing off the exit of the rectum by crushing the walls of the lower rectum into the walls of the anal canal with a liquid filled strap from only side of the rectum. Patent Application 2007/0073099 with inventors Forsell published on Mar. 29, 2007, discloses another mechanical device which forcibly seals the anus, but uses a more natural constriction which is circular in nature more closely aligned with the actual functions of the body. The application also discloses alternate adoptions of the device in relation to the rectum and the anal canal. These drastic surgical methods where devices are implanted within the patient's body are invasive and can cause a host of issues from infections and tearing of the sensitive tissues of the rectum and anus, causing even more damage to the anus, along with repeated mechanical crushing of the tissues to simulate the actions of the sphincter. These surgical techniques and solutions are not intended for everyone and only a small percentage benefit for a period of time from which then, the patient must seek alternative aids. Furthermore, these techniques require anywhere from 4 to 6 months to show some type of relief in selected patients.

The third basic categories of device that control anal leakage are devices that are fitted into the rectal cavity and anal canal. A study reported in the European Journal of Pediatrics Surgery in June of 2000 entitled "A new polyurethane anal plug in the treatment of incontinence after anal atresia repair" detailed the efficacy of plastic plugs inserted into the rectal cavity. The study found that the anal plug was the only nonsurgical treatment for fecal incontinence available to those patients who want to carry on a complete social life. U.S. Pat. No. 8,444,546 issued to Shalon et al on May 21, 2013 discloses two styles of anal plugs used to prevent incontinence. One style has an applicator inserting a "Y" shaped device which flattens out and seals against the walls of the anal canal. This problem with this style of device is that there is no means to control the position of the plug within the rectal area, let alone maintaining the position in the anal canal.. The British Journal of Nursing in November of 2004 discussed studies perform on a different style of anal plug called the Peristeen Anal Plug, developed originally as the Conveen Anal Plug, which is similar in design to the first iteration of the Shalon device. The journal discussed the positive results, but further clinical experience of others have found that this style of plug has no restriction on the migration of the plug deeper into the recesses of the rectum and further into bowel. There are no means to hold this device in the proper location, and as the user already has weakened or non-existent control of the sphincter muscles already, there is nothing to prevent the device from moving inward as the person moves and especially in the sitting position. In addition, the PU Conveen plug is not practical in the for of application. The user must use his/her fingers to properly insert the plug past the anal canal. This approach is unsanitary and discouraging for patients.

The second iteration of the Shalon patent discloses a plug that has a disk that has a diameter slightly greater than the anal canal, it is forced past the anus and both sphincter muscles, with either a two prong introducer or digitally placed, both of which have a much smaller diameter in relation to the diameter of the anal canal as shown in FIGS. 6B and 8C of Shalon. The other end of the plug has biasing cap which rests on the exterior of the anus. This biasing cap is to hold the plug in place, preventing the transiting of the plug further into the rectal cavity. The problem of maintaining location has been solved with a very draconian device in a very sensitive area. A person would have a stiff plastic unyielding stem or rod which is connected to a softer disc that have been forced past narrower canals in order to seal a larger canal in the sensitive anal canal. And since the stem connecting the two disks is not adjustable, the individual person is subjected to a norm to fit their particular body, subjecting the user to possible leakage past the lower seal should the connecting be too long for their particular body or the stem not thick enough to seal the anal canal itself. As the European Journal study did find that the plugs, even though made of a PVA or polyurethane material had painful inserts, due to the methods used to deploy these plugs, a feeling of uncomfortable pressure inside of the anal canal and painful plug removal due to the migration of the device inwardly and oversized plug as in the case of the PVA plug. Another study published in Cochrane Incontinence Group Specialized Register in 2012 found that anal plugs work if they can be tolerated and found that even though they are helpful in preventing incontinence, they can be difficult to tolerate due to the stiff and oversized material used. The group found that the rectal cavity must be trained over a few applications and with tolerable materials. The disposal of this device is also questionable as it would not be able to be flushed down the toilet forcing the user to deal with a bowel discharge while removing this device and making sure it does not go down the toilet, as well as having to find an appropriate disposal means.

It is an object of this invention to create a device that will prevent the anal leakage associated with incontinence. The device must be designed taking into account that every application is different in size and volume.

It is another object of this invention to create a device that will prevent anal leakage associated with incontinence that enables the person to carry on an active lifestyle without the worry of dislodgement or an embarrassing failure of the device, and furthermore, the device must provide comfort and flexible to prevent discomfort to the user.

It is further object of this invention to create a device that is comfortable in both the insertion, use and removal of said device from the very sensitive anal canal and rectal cavity, said device being developed with the knowledge that the insertion of the device will most likely be done by the user of the device. If nurse or caregiver is to apply device to patient, device allows for sanitary and non-digital intrusion for administration. This invention should not contain any sharp edges, or stiff connecting rods that cause discomfort, or places the user at risk for internal injury.

It is further object of this invention to allow the user to carry multiple units in a discrete fashion. The device is compact and can be carried in pant pocket or purse offering discretion and peace of mind knowing it's at their disposal.

Another object of this invention is to insure that the insertion means is never larger than the anus with minimal stretching of the anal canal during insertion.

It is a further object of this invention to create a device the is disposable and that can be removed and flushed down a toilet, reducing handling and disposal problems, since removal is likely to be associated with a bowel discharge. Good sanitary practice reduces the spread of microorganisms.

It is a further object of this invention to create a device that has application in all age groups and into fields beyond just human medicine, where animals can benefit from this device as the device should be easy to use, without painful insertion and prevent leakage in light of normal behavior.

It is a further object of this invention to have a device that has more than one sealing means to prevent anal leakage should the primary means not provide 100% protection.

It is a further object of this invention to have a device that has more than one functional means other than preventing anal leakage; it should also have a hemostatic benefit. On occasion post hemorrhoidectomy, some bleeding may occur internally in the proximal anal opening of internal anal canal region. Pressure placed on the internal region of bleeding area can reduce and cease the bleeding.

SUMMARY OF THE INVENTION

According to this invention in relation to the prior art discussed, this device for preventing anal leakage in those people who suffer from rectal incontinence is disclosed. This device is flexible and is non-invasive. There are no sharp corners, ridges or disks that are designed to hold the device in the proper location. The device has a proven leakage inhibitor or blocking capability which is deployed into the rectal cavity using a minimally intrusive deployment shield which is inserted into through the anal canal with an integrated stopping shoulder to allow the user the tactical feel of when to stop inserting and to deploy the device safely. The user uses a familiar motion of running the plunger to the maximum extent of its throw, as one would use a syringe. After the leakage inhibitor is deployed by using a plunger as acting as a deployment means, the user withdraws the shield and plunger in one motion exposing the external flapper and stopper which is adjacent to the intergluteal area as possible. This flapper provides a secondary means to prevent anal leakage. An embodiment of this invention includes a secondary internal flapper seal which is deployed along with the leakage inhibitor inside of the rectum. Due to the design of the plunger length, only the leak inhibitor and second internal flapper, if used, will be deployed and the sealing flapper will remain inside of the deployment shield. Withdrawal of the deployment shield and plunger allows for the external sealing flapper to be deployed and cinched against the anus. A small barrel-shaped stopper is cinched behind the sealing flapper to insure a good permanent seal. The flapper and leak inhibitor are connected via a flexible string or member, composed of cotton or synthetic materials such as rayon, said string continuing further past the stopper allowing the user to remove the device. The deployment shield and plunger are made of a recyclable plastic and the leak inhibitor and flapper are made of materials very similar in composition as female tampons.

BRIEF DESCRIPTION OF SEVERAL VIEWS OF THE DRAWINGS

In FIG. 1, shows the basic components of the device shown separated for clarification, from a left side front oblique view.

In FIG. 2, the deployment shield is shown from a frontal elevation.

In FIG. 3, the deployment shield is shown from a left side elevation where the plunger has been inserted to its maximum extent.

In FIG. 4, the deployment shield is shown in a rear elevation.

In FIG. 5, the deployment shield is shown from a lower rearward elevation where the plunger has been inserted to its maximum extent.

In FIG. 6, the plunger is shown in a side elevation.

In FIG. 7, the plunger is shown in a frontal elevation.

In FIG. 8, the plunger is shown in a rearward elevation.

In FIG. 9, the plunger is shown in a rearward left side lower oblique elevation.

In FIG. 10, the anti-reversing barrel stopper is shown in a frontal oblique view.

In FIG. 11, the barrel stopper is shown in a side elevation.

In FIG. 12, the barrel stopper is shown in a cross-sectional view from the cross-sectional line in FIG. 11.

In FIG. 13, the device is shown prior to its assembly in a cross-sectional view as the plunger is cross-sectioned through the external ribs.

In FIG. 14, the device is shown in its assembled condition in a cross-sectional view.

DETAILED DESCRIPTION OF THE INVENTION

Figure 16:
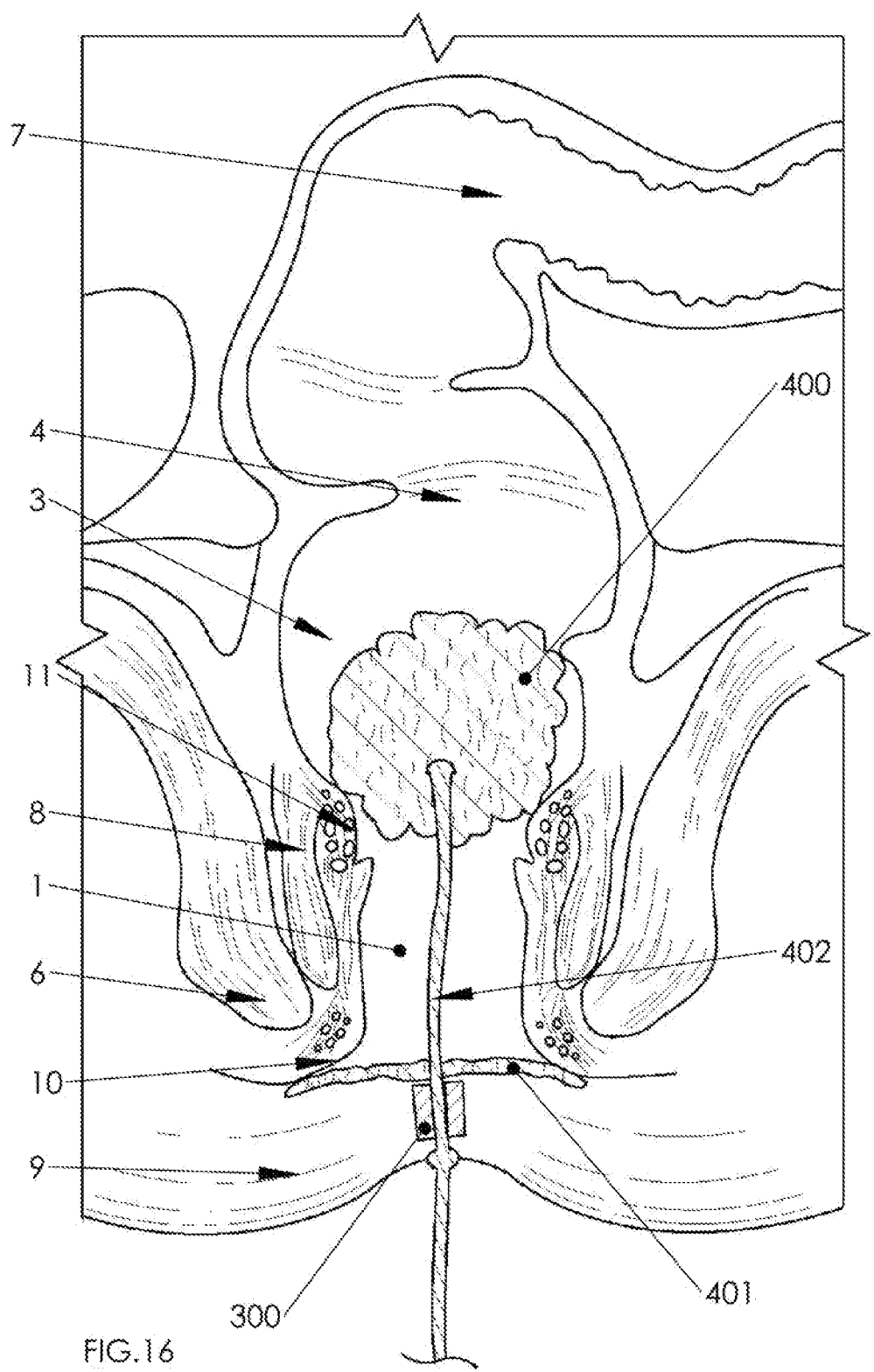
In FIG. 16, the device is deployed completely with the external sealing flapper being secured in the proper location and the flapper is held in position by the barrel stopper.

FIG. 1 shows the deployment shield and plunger in an exploded view. Shield 100 is consists of two principle regions; 1) deployment region 106 and 2) finger engagement area 101 which are separated by anus abutment 105. Abutment 105 has an anterior side 107 which has a slight reverse rake angle to accommodate a more comfortable fit into the intergluteal area and flush against the anus where the rearward side of stop 108 is generally perpendicular to the finger engagement area 101 to accommodate the flat distal side of the users fingers encompassing shield 100 and plunger 200 as the device is ready for insertion as seen in FIG. 14. It is critical that abutment 105 is located along shield 100 in a proper distance from the deployment ring 116 so that the device leakage inhibition means 400 (as shown in FIG. 16) is deployed into the anal cavity in the proper area, which is immediately superior to the interior anal sphincter and its set of muscular tissues in the anal canal. Deployment ring zone 116 is located on the distal end of shield 100 and is made up of multiple independent flanges 103, each being separated by flange gap 104 centered about deployment orifice 102. Flanges 103 emanate from distal end 112 of bore 116 and are radiused inwardly. Flanges 103 are designed to be sufficiently flexible to enable them to flex outwardly during deployment. This invention is made from a polyethylene or polypropylene material but should be noted that many style of plastic would be appropriate for use. It should be noted the all of the exposed edges of the flanges 103 are rounded without any sharp leading edges and the end of said flanges are radius inwardly to present a blunt end 117 of ring 116 which could decreases the possibility of damage to or piercing of, the tissues of the anal canal and rectal cavity. Rear finger gripping flange 110 is the most proximal place on shield 100 and upper surface 115 serves as the finger rest for the proximal side of the user's fingers. Flange 110 is generally elliptical in design which corresponds to the mid-digital gripping area of the anterior portion of the hand. The user's fingers are placed semi-circumferentially about grasping area 101 in a pronated orientation when the device is being used. The rearward surface 114 of flange 110 serves as a tactical stop for the user when the plunger is being inserted through the inner bore 116 of shield 100.

Plunger 200 has a hollow bore with an outer surface 203 and an inner surface 208, with a plunger travel stop 205 located proximally along outer surface 203 and a beveled channel 202 distally located terminating in a stepped ring 201. Plunger 200 has located thereupon it's outer surface 203, which allows space for flapper 401 to be securely positioned upon distal end of stepped ring 201, more than 4 ribs 204 whose purpose is to decrease the frictional surface area between the outer surface 203 of plunger 200 and the inner bore 116 of shield 100 as they are moved along the same axis. Plunger 200 is designed to be slidably related to shield 100, whereby the inner bore 116 of shield 100 accepts the outer surface 203 of plunger 200 where ribs 204 have a clearance fit known as a sliding fit, which is desirable for the plunger to rotate or slide freely within the inner bore of the shield. Stepped ring 201 has a hollow bore distal opening 209 located at the extreme distal end of plunger 200 and connects to the outer surface via a beveled channel 202. As seen in FIG. 13, ribs 204 has a tampered leading edge 207 which tampers into the outer surface 203. The purpose of ring 201 is to hold the sealing flapper 401 in place and to deploy the leak inhibitor means 400. The larger the flapper 401, there will be a greater need to have a location whereby the flapper is able to stored and thus a second stepped surface might be required. Flapper 401 is generally rectangular in shape in order to fit into the intergluteal area and flush against the anus. The width or minor side of the rectangular shape of flapper 401 is greater than the diameter of the user's anus. As with the shield 100, plunger 200 is made from a polyethylene or polypropylene material but should be noted that many style of plastic would be appropriate for use.

Barrel stopper 300 has an outer surface 302 which thereupon it's common axis are multiple protuberances 303, whose purpose is to facilitate a better grip for the user, though a smooth bore can be used. Inner bore 302 contains multiple gripping means 304. One embodiment has multiple beveled gripping teeth 305 with interiorally beveled triangular sides 306 and 308 with a central vertex 309 terminating in vertex point 307. This designed to allow for travel along connecting member 402 in a singular direction with minimal resistance, and will grip into said member 402 when the direction of travel is reversed. Barrel stopper 300 can be made of a softer material, such as a silicone or polyvinyl chloride.

FIGS. 13 and 14 detail the shield and plunger in preparation for use. FIG. 13 is a cross-sectional view whereby connecting member 402, whose composition can be cotton or synthetic fibers, is shown where leakage inhibitor 400 is located at the distal end of said member 402, securely attached thereto, and member 402 is positioned with inhibitor 400 along inner bore 116 of shield 100. Plunger 200 has sealing flapper 401 placed over step 201 with member 402 being threaded through the middle of flapper 401 and stopper 300 prior to entering the inner surface 208 of plunger 200 through bore opening 209. Stopper 300 is threaded through by member 402 and is located within the bore opening 209. Threaded knot 403 serves as a release preventer, whereby barrel 300 cannot transit any further down member 402 and prevents disassembly of the product during assembly, packaging or use. It should be noted that the length of plunger is limited by the inner bore of the shield as well as being of such length as to be shorter than the inner bore of shield 100. This shortness allows for the deployment of the leakage inhibitor through flanges 103 but is not long enough to deploy flapper 401 in the same deployment. The plunger is designed to be too short to deploy the flapper into the anal canal as travel stop 205 will prevent any further travel of the plunger into the shield. FIG. 14 shows the device assembled as ready for packaging. Since this product is not required to be sterile, there are no step sterilization steps after assembly. The material composition of the leakage inhibitor means 400 is similar in composition to a female tampon, having an internal material using cotton, rayon, or a blend of both materials. Rayon is a synthetic product made from cellulose, generally made from wood pulp, which is bio-degradable along with cotton. The interior material is surrounded by an absorbent cover often made of polyester/polyethylene non-woven material.

Figure 15:
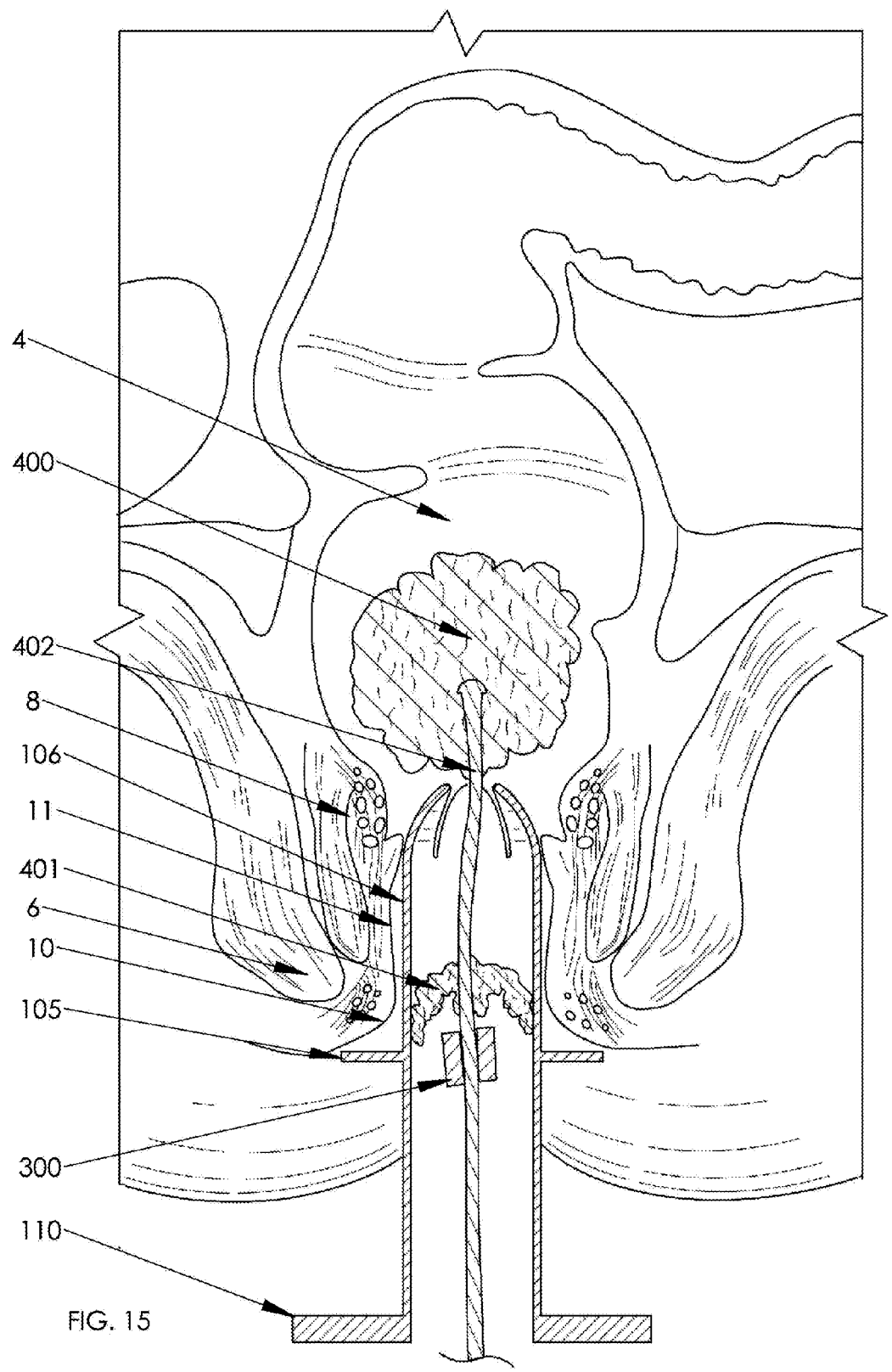
In FIG. 15, the deployment shield is inserted into the rectal cavity and the leakage inhibitor has been deployed from the device and the plunger has been withdrawn.

FIG. 15 shows the shield of the device after insertion into the anal canal 1 past the anus 10 and the upper 6 and lower sphincter 6 muscles. As per procedure, the plunger has been completely engaged into the shield causing the deployment of the leaking inhibitor 400 into the ampulla recti 3 inside of rectum 4. The shield anus abutment 105 has prevented further insertion is it rests upon opening of anus 10 preventing deployment within colon 7. FIG. 15 shows that the plunger 200 has been removed to illustrate the contents therein and flapper 401 and stopper 300 are located along the inner bore 116. However in practice, both shield 100 and plunger 200 will be removed simultaneously in one motion. The user has inserted the shield and plunger assembly through the anus and into the rectal canal after preferably using an anal or petroleum based lubricant upon the deployment ring 116. User has inserted the shield up to stop 105 and has positioned the middle finger and thumb of their dominant hand, in a pinching fashion on grasping area 101 with the user's index finger of the same hand articulated about plunger stop 205. Using a co-planar pinching motion, the user brings their index finger next to the opposing finger and thumb moving the plunger the maximum distance where stop 205 meets the exterior surface 116 of shield 100, thereby deploying the leakage inhibitor 400 without deploying flapper 401. Inhibitor 400 is now in position immediately distal to the anal canal in the inferior rectum. The user then withdraws the shield 100 and plunger 200 in one motion, thereby exposing the seal flapper 401 as seen in FIG. 15. FIG. 16 shows the device in place with the removal of shield 100 and the flapper 401 securely held in position by stopper 300 against the anus 10, guarding against any leakage that could possibly get past inhibitor 400 as a second line of defense, and the remaining portion of the connecting member 402 hangs down below the gluteus Maximus 9 allowing for the user to have access to grasp the member 402 for removal. This remaining portion is referred to as the removal distance, and should be of a length as to permit users of various girths and flexibility to be able to grasp and removal the device. As seen in FIG. 16, the device is securely located in the inferior rectum blocking the anal canal where the inhibitor will naturally expand and absorb. Flapper 401 provides for the second stage of protection against anal leakage in this device.

Figure 17:
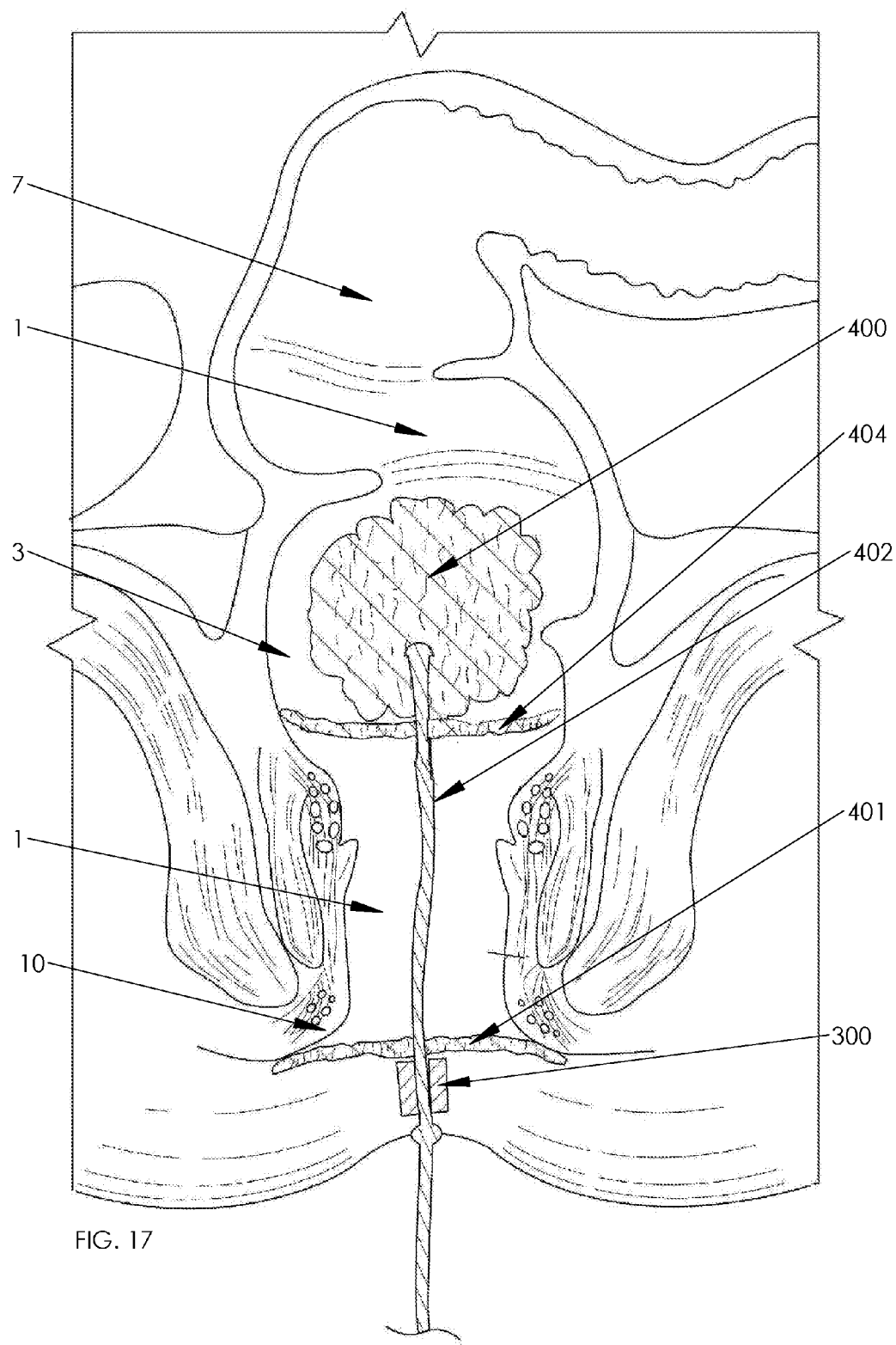
In FIG. 17, an embodiment of this invention is shown where a secondary flapper is engaged next to the leakage inhibitor providing a secondary layer of protection from leakage.

FIG. 17 discloses an embodiment of the invention as it shows the addition of a circular sealing disc 404. This will be the second line of defense to prevent leakage prior to sealing flapper 401. Disc 404 will be deployed with the leakage inhibitor 400 and is placed in between the proximal anal canal 11 and the leakage inhibitor 400 which will be in the proximal rectal cavity. Disc 404 will create a seal about the distal end of anal canal which is naturally smaller in diameter than the proximal end of the rectal cavity. Disc 404 is greater in diameter than inhibitor 400 and provide a larger sealing area against the opening of the anal canal. As seen in FIG. 17, the leakage inhibitor and the secondary disc 404 are securely located in the inferior rectum blocking the anal canal where the inhibitor will naturally expand and seal against the narrow opening of the distal end of the anal canal. The disc 404 is the secondary sealing means or second line of defense sealing against the internal proximal anal canal to prevent any leakage that has not been absorbed by leakage inhibitor 400. Disc 404 is constructed of a material similar in composition to sealing flapper 401. In this invention, disc 404 and flapper 401 were constructed using cotton or synthetic fibers such as Rayon, but this invention is not limited to those materials as other material can be proven to work as effectively as these materials. This embodiment provides three stages of leakage protection.

Removal of the device is accomplished by securely grasping the member 402 and firmly pulling, while bearing down slightly as if defecating, until the inhibitor 400 safely transits the anal canal and the device can fall into the toilet along with the evacuated fecal matter that has been securely held in place.

It can be appreciated by those appropriately skilled in the art that changes, modifications or embodiments can be made to this invention without departing from the spirit, principles, theories, ideas or conceptions that have been disclosed in the foregoing. It is herein recognized that the embodiments disclosed by this description are included as part the best mode of practicing this invention, which will be hereafter described in their full breadth in the claims and equivalents thereof.

What is claimed is:

1. A device to avert anal fecal leakage comprising:
  a shield, defined as being cylindrical hollow core about an external shell having a central axis, said shell having a proximal bottom flange, elliptical in shape and a circular anus abutment stop, distally related to said bottom flange and circumferentially encompassing said shell and a deployment ring zone, said zone located a pre-determined distance distally of said abutment, said pre-determined distance approximately corresponding to the distance from the anus to the inferior rectal cavity of the user, said zone having a rounded blunt exterior and a corresponding interior;
  a leakage inhibitor means, capable of placement into said deployment ring zone of said hollow core of said shield through said bottom flange and relocated distally into said interior of said deployment ring;
  a sealing flapper, having a centrally located aperture, having an upper sealing region and a lower engagement region, said upper sealing region being proximally located to said leakage inhibitor means;
  a connecting member, having a distal portion to which is secured said leakage inhibitor and passing through said aperture of said flapper entering along said upper sealing region and exiting through said lower engagement region;
  a securing stopper, being cylindrical in shape having an outer diameter greater than said aperture of said flapper and located adjacent to said lower engagement region of said flapper, said stopper being designed to easily permit one way travel distally along said connecting member with resistance to travel anteriorly along said connecting member; and
  a plunger, defined as being cylindrical bore about an circular external surface having the same central axis as said shield where said surface has a radius less than the radius of said bore of said shield allowing for said slidable engagement of said plunger and said hollow core of said shield.

2. A device to avert anal fecal leakage as in claim 1 where said external surface of said plunger contains multiple protuberances aligned along said central axis, said protuberances designed to minimize friction during slidable engagement of said shield and said plunger, said protuberances creating a sliding fit between said protuberances and said hollow core of said shield.

3. A device to avert anal fecal leakage as in claim 1 where said external surface of said plunger having a distal beveled receiving end, designed to receive said sealing flapper and a proximal travel stop preventing further travel of said plunger into said shield, said plunger bore being adapted to allow for said connecting member to transit therethrough, where the interior bore of said beveled receiving end is designed to be greater than the outside dimension of said connecting member and less than the outside diameter of said sealing stopper.

4. A device to avert fecal leakage as in claim 1 where said connecting member of a sufficient measurement to transit length of said shield and said plunger and an additional removal distance located proximal end of said connecting member.

5. A device to avert fecal leakage as in claim 1 where said sealing flapper is shaped to seal against the exterior shape of the user's anus where said flapper seals upon the anus.

6. A device to avert anal fecal leakage as in claim 1 where said securing stopper being designed to easily permit one way travel distally along said connecting member with resistance to travel anteriorly along said connecting member.

7. A device to avert anal fecal leakage as in claim 1 where said deployment ring zone contains multiple interiorly radiused flanges that emanate independently along entire circumference of said hollow core from said distal end of said shield, where said flanges are separated from each other by a consistent flange gap at all places along said flange, where said flanges terminate distally allowing a centrally located deployment orifice.

8. A device to avert fecal leakage as in claim 1 where said leakage inhibitor means comprises a cotton or Rayon core loosely surrounded by a thin porous absorbent netting, said core being sufficient in size as to expand and seal against the inferior rectal wall as it narrows into the anal canal.

9. A device to avert fecal anal fecal leakage as in claim 5 where said sealing flapper is shaped in a rectangular fashion whose minor sides are greater in length than the diameter of the anus to be sealed.

10. A method of using the device to avert fecal leakage of a subject comprising the steps of;
  Obtaining the device as disclosed in claim 1,
  Opening any packaging associated with said device,
  Applying a lubricant to distal end of device,
  Inserting device through the anus and into the rectal cavity until the circular anal abutment stop engages against the exterior portion of the anus,
  Deploying anal leakage inhibitor means by engaging plunger portion of said device into the shield portion of said device using a co-planar pinching motion into the inferior rectum cavity,
  Withdrawing said shield and said plunger, thereby deploying a sealing flapper and barrel stopper which are in communication with said anal leakage inhibitor using a connecting member,
  Cinching said barrel stopper upwardly along said connecting member, firmly positioning said leakage inhibitor in said inferior rectal cavity against said distal end of said anal canal and securing said sealing flapper against the exterior of the anus, Using the device to prevent anal leakage by the subject, Removing said device by having the user bear down and pull on exposed end of said connecting member until device is evacuated, and Disposing of said device.

11. A method of using the device to avert fecal leakage of a subject as in claim 10 where removal of disposal of said device can be accomplished using a sanitation fixture used primarily for the disposal of human excrement said fixture being connected to a septic system or a sewerage pipe system.

12. A device to avert anal fecal leakage comprising:

a shield, defined as being cylindrical hollow core about an external shell having a central axis, said shell having a proximal bottom flange, elliptical in shape and a circular anus abutment stop, distally related to said bottom flange and circumferentially encompassing said shell and a deployment ring zone located a pre-determined distance distally of said abutment, said pre-determined distance approximately corresponding to the distance from the anus to the inferior renal canal of the user, said zone having a rounded blunt exterior and a corresponding interior;

a leakage inhibitor means, capable of placement into said deployment ring zone of said hollow core of said shield through said bottom flange and relocated distally into said interior of said deployment ring;

a sealing disc, having a centrally located orifice, said disc being circular in shape, having a diameter greater than the diameter of the user distal anal cavity, said disc designed to be capable of placement immediately adjacent to said leakage inhibitor means in said deployment ring zone, a sealing flapper, having a centrally located aperture, having an upper sealing region and a lower engagement region, said upper sealing region being proximally located to said leakage inhibitor means;

a connecting member, having a distal portion to which is secured said leakage inhibitor and passing through said orifice of said sealing disc and said aperture of said flapper entering along said upper sealing region and exiting through said lower engagement region;

a securing stopper, being cylindrical in shape having an outer diameter greater than said aperture of said flapper and located adjacent to said lower engagement region of said flapper, said stopper being designed to easily permit one way travel distally along said connecting member with resistance to travel anteriorly along said connecting member; and a plunger, defined as being cylindrical bore about an circular external surface having the same central axis as said shield where said surface has a radius less than the radius of said bore of said shield allowing for said slidable engagement of said plunger and said hollow core of said shield.

13. A device to avert anal fecal leakage as in claim 12 where said external surface of said plunger contains multiple protuberances aligned along said central axis, said protuberances designed to minimize friction during slidable engagement of said shield and said plunger, said protuberances creating a sliding fit between said protuberances and said hollow core of said shield.

14. A device to avert anal fecal leakage as in claim 12 where said external surface of said plunger said plunger having a distal beveled receiving end, designed to receive said sealing flapper and a proximal travel stop preventing further travel of said plunger into said shield, said plunger bore being adapted to allow for said connecting member to transit therethrough, where the interior bore of said beveled receiving end is designed to be greater than the outside dimension of said connecting member and less than the outside diameter of said sealing stopper.

15. A device to avert fecal leakage as in claim 12 where said connecting member of a sufficient measurement to transit length of said shield and said plunger and an additional removal distance located proximal end of said connecting member.

16. A device to avert fecal leakage as in claim 12 where said sealing flapper is shaped to seal against the exterior shape of the user's anus where said flapper seals upon the anus or as far inside of the intergluteal area as possible and where said sealing flapper is constructed of a cotton or Rayon material rectangular in shape.

17. A device to avert anal fecal leakage as in claim 12 where said securing stopper being designed to easily permit one way travel distally along said connecting member with resistance to travel anteriorly along said connecting member.

18. A device to avert anal fecal leakage as in claim 12 where said deployment ring zone contains multiple interiorly radiused flanges that emanate independently along entire circumference of said hollow core from said distal end of said shield, where said flanges are separated from each other by a consistent flange gap at all places along said flange, where said flanges terminate distally allowing a centrally located deployment orifice.

19. A device to avert fecal anal fecal leakage as in claim 12 where said leakage inhibitor means comprises a cotton or Rayon core loosely surrounded by a thin porous plastic netting, said core being sufficient in size as to expand and seal against the inferior rectal wall as it narrows into the anal canal while said sealing disc, having a greater diameter than said core, providing the secondary means of preventing leakage by also sealing against the inferior rectal wall.

20. A method of using the device to avert fecal leakage of a subject comprising the steps of;

Obtaining the device as disclosed in claim 12,

Opening any packaging associated with said

Applying a lubricant to distal end of device,

Inserting device through the anus and into the rectal cavity until the circular anal abutment stop engages against the exterior portion of the anus, Deploying anal leakage inhibitor means and sealing disc by engaging plunger portion of said device into the shield portion of said device using a co-planar pinching motion into the inferior rectum cavity, Withdrawing said shield and said plunger, thereby deploying a sealing flapper and barrel stopper which are in communication with said anal leakage inhibitor and said sealing disc using a connecting member, Cinching said barrel stopper upwardly along said connecting member, firmly positioning said leakage inhibitor and said sealing disc in said inferior rectal cavity against said distal end of said anal canal and securing said sealing flapper against the exterior of the anus, Using the device to prevent anal leakage by the subject, Removing said device by having the user bear down and pull on exposed end of said connecting member until device is evacuated, Disposing of said device using a sanitation fixture used primarily for the disposal of human excrement said fixture being connected to a septic system or a sewerage pipe system.

* * * * *